(12) United States Patent
Bellrichard et al.

(10) Patent No.: US 10,525,247 B2
(45) Date of Patent: Jan. 7, 2020

(54) LEAK REDUCTION DURING IMPLANTABLE INFUSION DEVICE REFILL

(71) Applicant: Medtronic, Inc., Minneapolis, MN (US)

(72) Inventors: Mark A. Bellrichard, Champlin, MN (US); Brian W. Ball, Maple Grove, MN (US); Kenneth J. Kahle, Cedar, MN (US); Mary M. Morris, Shoreview, MN (US); Michael P. Piette, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 654 days.

(21) Appl. No.: 14/825,633

(22) Filed: Aug. 13, 2015

(65) Prior Publication Data
US 2017/0043151 A1 Feb. 16, 2017

(51) Int. Cl.
*A61M 39/02* (2006.01)
*A61M 5/142* (2006.01)
*A61M 5/44* (2006.01)

(52) U.S. Cl.
CPC .... *A61M 39/0208* (2013.01); *A61M 5/14276* (2013.01); *A61M 5/44* (2013.01);
(Continued)

(58) Field of Classification Search
CPC .......... A61M 39/0208; A61M 39/0247; A61M 5/14276; A61M 5/44; A61M 2205/3606; A61M 2039/0276; A61M 5/1483; A61M 5/1486; A61M 2205/04; A61M 2039/0211; A61M 2039/0214; A61M 2039/0217; A61M 2039/022; A61M 2039/0223; A61M 2039/0226; A61M 2039/0229; A61M 2039/0232; A61M 2039/0235; A61M 2039/0238; A61M 2039/0241; A61M 2039/0244; A61M 2039/025; A61M 2039/0252; A61M 2039/0255; A61M 2039/0258; A61M 2039/0261; A61M 2039/0264; A61M 2039/0267; A61M 2039/027; A61M 2039/0273; A61M 2039/0279; A61M 2039/0282; A61M 2039/0285; A61M 2039/0288; A61M 2039/0291; A61M 2039/0294; A61M 2039/0297
See application file for complete search history.

(56) References Cited

U.S. PATENT DOCUMENTS

| 3,731,681 A | 5/1973 | Blackshear et al. |
| 3,951,147 A | 4/1976 | Tucker et al. |

(Continued)

FOREIGN PATENT DOCUMENTS

| EP | 0488701 A1 | 3/1992 | |
| WO | WO 97/40873 A1 | 11/1997 | |
| WO | WO 2014184358 A2 * | 11/2014 | ........ A61M 5/16831 |

OTHER PUBLICATIONS

PCT Patent Application No. PCT/US2016/046731, filed Aug. 12, 2016; International Search Report / Written Opinion dated Nov. 4, 2016; 14 pages.

(Continued)

*Primary Examiner* — Kami A Bosworth
*Assistant Examiner* — Alexandra Lalonde
(74) *Attorney, Agent, or Firm* — Mueting, Raasch and Gebhardt, P.A.

(57) ABSTRACT

A method for reducing small volume subcutaneous leaks of therapeutic fluids during procedures to refill an implantable medical device includes reducing pressure in a reservoir of the device. A refill needle can be percutaneously inserted into a fill port in communication with the reservoir and therapeutic fluid can be delivered through the needle into the reservoir. Reduced reservoir pressure upon withdrawal of the refill needle from the port can result in reduced subcutaneous leakage of the therapeutic fluid.

13 Claims, 4 Drawing Sheets

(52) U.S. Cl.
CPC . *A61M 39/0247* (2013.01); *A61M 2039/0244* (2013.01); *A61M 2039/0273* (2013.01); *A61M 2039/0276* (2013.01); *A61M 2205/04* (2013.01); *A61M 2205/3606* (2013.01)

(56) References Cited

U.S. PATENT DOCUMENTS

| | | |
|---|---|---|
| 5,167,633 A | 12/1992 | Mann et al. |
| 6,280,416 B1 | 8/2001 | Van Antwerp et al. |
| 8,672,917 B2 | 3/2014 | Sigg et al. |
| 8,790,295 B1 | 7/2014 | Sigg et al. |
| 2007/0016171 A1* | 1/2007 | Podvin .................. A61M 5/141 604/891.1 |
| 2007/0255227 A1 | 11/2007 | Haase |
| 2009/0082757 A1 | 3/2009 | Rogers et al. |
| 2009/0270844 A1 | 10/2009 | Seeley et al. |
| 2011/0196294 A1 | 8/2011 | Forsell |
| 2012/0265141 A1* | 10/2012 | Kalpin .............. A61M 5/14276 604/131 |

OTHER PUBLICATIONS

Remodulin Product Information, Feb. 2008, available at https://www.accessdata.fda.gov/drugsatfda_docs/label/2008/021272s009lbl.pdf (last visited Oct. 11, 2018).

\* cited by examiner

LEAK REDUCTION DURING IMPLANTABLE INFUSION DEVICE REFILL

FIELD

This disclosure generally relates to, among other things, implantable medical infusion devices; and more particularly to implantable infusion devices that have positive pressure reservoirs and methods for reducing leakage of therapeutic fluid during procedures to refill the positive pressure reservoirs.

BACKGROUND

A variety of therapies exist for treating patients with implantable infusion systems. The implantable infusion systems can be used to deliver therapeutic fluids to a target location of a patient, such as the spinal canal, the brain, or the heart. The implantable infusion systems include implantable infusion devices that are often subcutaneously implanted in a convenient location in the patient and implantable catheters that are used to carry the therapeutic fluids from the infusion device to the target location.

Implantable infusion devices can have refillable reservoirs for housing the therapeutic fluids, which can be infused over time. The reservoirs can be periodically refilled so that the implanted infusion systems can be employed for long-term use. Typically, the infusion devices have a fill port in communication with the reservoir. A refill apparatus needle can be percutaneously inserted into the fill port so that fresh therapeutic fluid can flow through the refill needle into the port to refill the reservoir and replenish the supply of therapeutic fluid.

Because the device is implanted within the patient and cannot be seen directly, care must be taken to ensure that the needle is properly placed into the port before transferring the therapeutic fluid. If the needle is not properly located within the fill port, the therapeutic fluid may be inserted into a subcutaneous pocket of the patient rather than into the reservoir of the implanted infusion device. Accordingly, efforts have been made to identify to a clinician the location of the fill port relative to the patient's skin prior to insertion of the refill needle. For example, templates are well known, and can provide a general indication or map of the port assembly location following palpating the device's periphery through the patient's skin. Additionally, electronic or magnetic systems have been suggested that provide the clinician with additional information generally indicative of the port position. Once the clinician arrives at an initial estimation of port location, upon inserting the needle through the patient's skin, the clinician normally can make a manual tactile determination as to whether the needle tip has been correctly directed to the appropriate port and has subsequently pierced through a septum covering the port. Most clinicians are relatively comfortable in making this determination as, based on experience; the clinician can tactilely sense or feel when the needle has been inserted through the septum. As such, accidental subcutaneous "pocket fills" are rare.

SUMMARY

It has been found that small amounts of therapeutic fluid can leak from a refill needle during a procedure to refill a reservoir of the device via the port. This can occur despite proper insertion of the refill needle into the fill port. Depending on factors such as the drug in the therapeutic fluid, concentration of the drug, and the sensitivity of the patient, small amounts of subcutaneous leakage can result in no adverse reaction, a local reaction such as redness or pain in the subcutaneous tissue near the refill site, a systemic reaction such as flushing or nausea, or other adverse reactions. Devices, methods and systems for reducing the incidence or volume of such leakage during procedures to refill the reservoir of the infusion device are described herein.

In some embodiments described herein, methods for reducing leakage of therapeutic fluid during a refill procedure include reducing pressure in the reservoir and inserting fluid into the reservoir. The pressure can be reduced as the fluid is introduced, prior to introduction of the fluid, or after the fluid is introduced. Preferably, the pressure in the reservoir is reduced to a pressure below 0 psig to temporarily create a negative gauge pressure in the reservoir.

Leakage events have been observed when refilling a reservoir under positive pressure when using a refill kit that includes an extension set having a compliant catheter. Without intending to be bound by theory, it is believed that, because the refill needle and extension set catheter are in communication with the positive pressure reservoir, the needle and catheter are under positive internal pressure as the needle is withdrawn from the port. The change to ambient pressure upon withdrawal of the needle into subcutaneous tissue can cause a small volume of therapeutic fluid to leak from the needle into the patient. By changing the pressure in the reservoir to relative negative pressure, the pressure in the needle and catheter will be negative as the needle is withdrawn from the port into ambient pressure subcutaneous tissue. Due to the relative negative pressure in the needle, a residual drop or volume of therapeutic fluid, if present, may be aspirated into the needle rather than into the subcutaneous tissue of the patient.

Some embodiments of the methods described herein may thus be particularly advantageous when employed with implantable infusion devices having positive pressure reservoirs.

In some embodiments described herein, methods for reducing leakage of therapeutic fluid during a refill procedure include percutaneously introducing a therapeutic fluid into a reservoir of an implantable medical device. The temperature of the therapeutic fluid being introduced is 20° C. or less, such as 10° C. or less, or about 5° C. By introducing a fluid having a reduced temperature into the reservoir, pressure in the reservoir can be reduced. The introduction of low temperature therapeutic fluids into a reservoir under a positive pressure due to a propellant can be particularly effective at lowering pressure in the reservoir if introduction of the fluid in the reservoir cools the propellant.

In some embodiments described herein, an implantable medical device includes a chamber, a reservoir, a propellant and a cooler. At least a portion of the reservoir is disposed in the chamber. The propellant is disposed in the chamber, exterior to the reservoir, and exerts a pressure elevating force on the reservoir. The cooler is positioned and configured to cool the propellant to reduce pressure in the reservoir during a procedure to fill the reservoir.

In some embodiments, a method for reducing incidence of side effects associated with refilling a reservoir of an implantable infusion device with treprostinil sodium is described. The method includes identifying a patient having an implanted infusion device. The infusion device includes a positive pressure reservoir and includes a propellant exerting pressure on the reservoir. The patient is receiving treatment with a fluid therapeutic that includes treprostinil sodium. The fluid therapeutic is infused fluid from the reservoir of the implanted infusion device into the patient. The method further includes percutaneously removing the therapeutic fluid from the reservoir, if any of the therapeutic fluid remains in the reservoir. The method also includes percutaneously refilling the reservoir with fresh therapeutic fluid comprising treprostinil sodium, wherein the temperature of the fresh therapeutic fluid being introduced is less than 10° C.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, in which.

Figure 1:
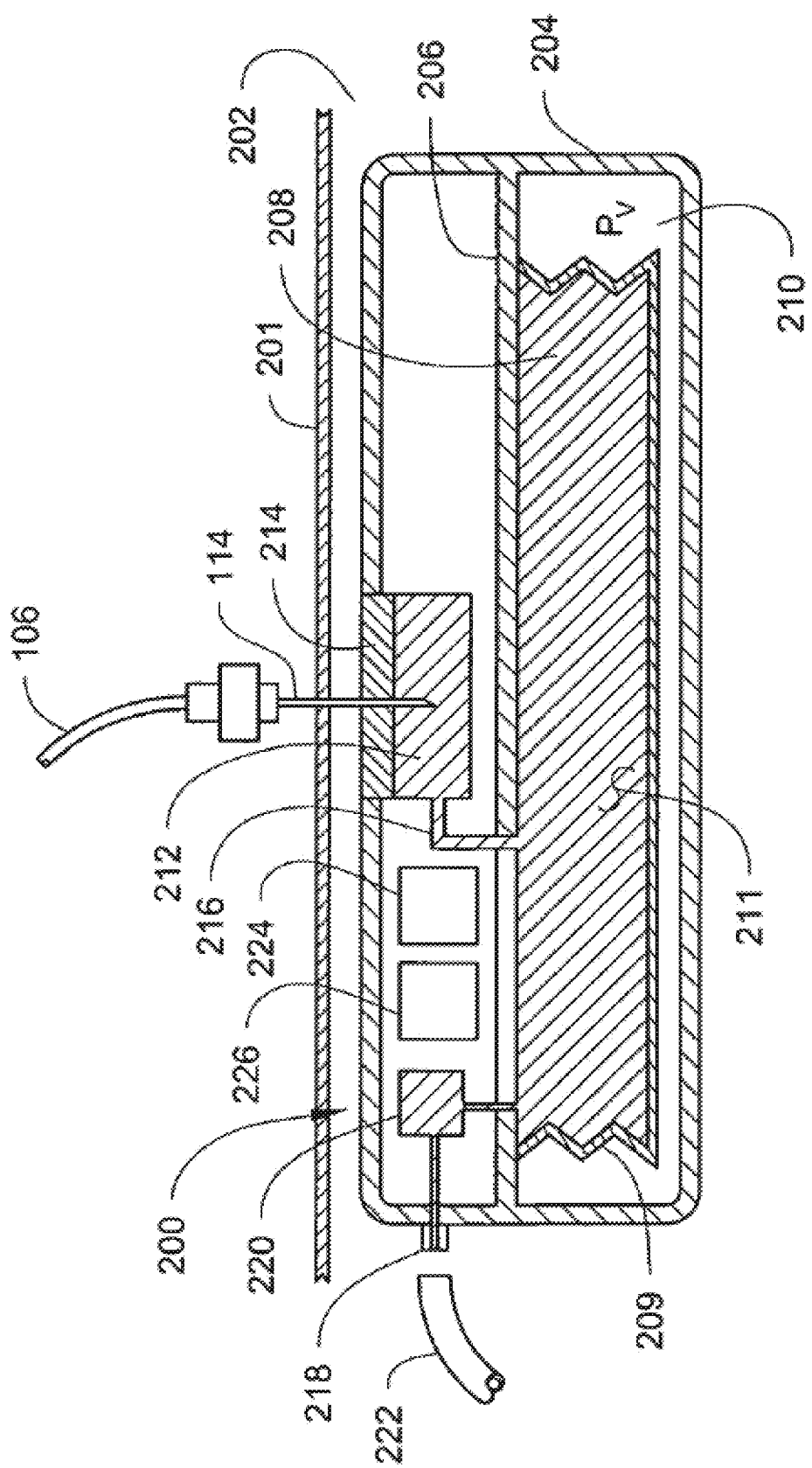
FIG. 1 is a schematic cross-sectional view of an embodiment of an implantable infusion device that can be used in accordance with some embodiments of the teachings presented herein.

The schematic drawings in are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

This disclosure describes, among other things, methods and devices for reducing leaks from a refill needle or a fill port of an implantable infusion device during procedures to refill a reservoir of the infusion device.

It has been found that withdrawal of a refill needle from a refill port after introduction of therapeutic fluid through the needle into a reservoir via the port can result in small amounts of therapeutic fluid subcutaneously leaking from the needle. For example a small percentage of reservoir refills resulted in an adverse reaction in a clinical trial for treatment of pulmonary arterial hypertension (PAH) by intravascularly delivering Remodulin® (treprostinil) Injection, (1R,2R,3aS,9aS)-[[2,3,3a,4,9,9a-Hexahydro-2-hydroxy-1-[(3S)-3-hydroxyoctyl]-1Hbenz[f]inden-5-yl]oxy] acetic acid, via a Medtronic, Inc. SynchroMed® II programmable infusion device. The refill reaction varied from local-only reaction of redness and pain in the subcutaneous tissue at the pump near the refill site, to a systemic reaction of flushing, nausea, and hypotension resulting in emergency medical monitoring and management. These symptoms are consistent with subcutaneous delivery of Remodulin® (treprostinil) Injection with severity related to dose response. Investigation of this issue resulted in a conclusion that Remodulin® (treprostinil) Injection was leaking from the needle during withdrawal of the needle from the port towards the end of the refill process.

The volume of Remodulin® (treprostinil) Injection that subcutaneously leaked was likely very small and is believed to be about 0.05 ml or less. However, at the concentration used (10 mg/ml), a subcutaneous dose of about 0.04 ml could result in a decrease in systolic blood pressure from 120 mmHg to 80 mmHg.

The reservoir of a Medtronic, Inc. SynchroMed® II programmable infusion device is a positive pressure reservoir. The pressure in a full reservoir of the SynchroMed® II programmable infusion device typically is in a range from about 2 psig to about 5 psig.

Interestingly, adverse events due to small leakage of therapies that involve delivering morphine or baclofen using the SynchroMed® II programmable infusion device have not been reported despite such therapies being employed for many years. This could be due to lack of adverse reaction to subcutaneous delivery of baclofen an morphine in the general population compared to adverse reaction in about 85% of the population to subcutaneous treprostinil administration. Another cause of adverse event with small volume delivery of therapeutic fluid containing treprostinil could be the bioequivalence of subcutaneous treprostinil and intravascular treprostinil. Such subcutaneous bioequivalence is not observed with intrathecal baclofen or morphine.

While the methods, systems and devices described herein may be more beneficially employed with therapeutic compositions that include a drug that elicits an adverse reaction when administered subcutaneously or that has bioequivalence, or near bioequivalence, when delivered subcutaneously as compared to its intended route of administration, the methods, systems and devices described herein can be employed with any fluid therapeutic composition deliverable by an implantable infusion device. For example, the methods, systems and devices described herein can be employed with a fluid therapeutic composition that includes baclofen, morphine, insulin, or any other drug currently used with implantable infusion systems or that may be used with implantable infusion systems in the future.

In some embodiments, the methods, systems and devices described herein can be employed with a fluid therapeutic composition that includes a drug for treating hypertension. In some embodiments the anti-hypertensive drug is useful for treatment of pulmonary arterial hypertension (PAH). Examples of drugs that can be used to treat hypertension include endothelin receptor antagonists, phosphodiesterase type 5 inhibitors, and a prostanoids. Representative examples of some of these types of compounds include bosentan [4-tert-butyl-N-[6-(2-hydroxyethoxy)-5-(2-methoxyphenoxy)-2-(pyrimidin-2-yl)pyrimidin-4-yl]benzene-1-sulfonamide]; silendafil [1-[4-ethoxy-3-(6,7-dihydro-1-methyl-7-oxo-3-propyl-1H-pyrazolo[4,3-d]pyrimidin-5-yl)phenylsulfonyl]-4-methylpiperazine]; iloprost [(E)-(3aS,4R, 5R, 6aS)-hexahydro-5-hydroxy-4-[(E)-(3S,4R)-3-hydroxy-4-methyl-1-octen-6-ynyl]-$\Delta^{2(1H),\Delta}$-pentalenevaleric acid]; treprostinil [(1R,2R,3aS,9aS)-[[2,3,3a,4,9,9a-Hexahydro-2-hydroxy-1-[(3S)-3-hydroxyoctyl]-1Hbenz[f]inden-5-yl]oxy]acetic acid]; and epoprostenol [(5Z,9α,11α,13E,15S)-6,9-epoxy-11,15-dihydroxyprosta-5,13-dien-1-oic acid]. In some embodiments, a therapeutic fluid comprises treprostinil sodium.

The methods, systems and devices described herein can be used with, or have, any suitable reservoir. In various embodiments, the methods, systems and devices described herein are used with, or have, a positive pressure reservoir. A positive pressure reservoir is a reservoir that has an internal gauge pressure of greater than zero under standard implanted operating conditions (e.g., 37° C.) when the reservoir is filled with therapeutic fluid to its operating capacity. In many cases, the pressure in the reservoir, when the reservoir is filled to half its full operating capacity, will be the same or nearly the same (e.g., within about 20%) as the pressure in the reservoir when the reservoir is filled to its operating capacity with therapeutic fluid. In various embodiments, a positive pressure reservoir, when full, has a gauge pressure of greater than 1 psig. In some embodiments, a positive pressure reservoir, when full, has a gauge pressure of between 1 psig and 30 psig, such as in a range from 2 psig to 10 psig or from 3 psig to 5 psig.

In some embodiments an infusion device includes a positive pressure reservoir disposed in a chamber having a propellant disposed in the chamber, external to the reservoir, and exerting a force on the reservoir. Any suitable variable volume reservoir can be used. For example, the reservoir can be formed from a collapsible bag, an elastic bladder, a bellows, or the like. Preferably, the interior volume of the reservoir, in the absence of external forces (such as propellant) would be at or near ambient pressure.

Examples propellant chambers and variable volume reservoirs that can be used in accordance with the teachings presented herein include those disclosed in U.S. Pat. Nos. 3,731,681; 3,951,147; and 5,167,633, which are hereby incorporated herein by reference in their entireties to the extent that they do not conflict with the disclosure presented herein.

An infusion device can include any suitable propellant or propellant mixture that has a vapor pressure above ambient pressure at 37° C. Preferably, the propellant or propellant mixture has a substantially reduced vapor pressure at a lower temperature, such as at 10° C. In some embodiments, the internal pressure of the reservoir decreases when therapeutic fluid having a temperature of about 20° C. or less, such as about 10° C. or less or about 5° C., is introduced into the reservoir due, at least in part, to cooling of the propellant or propellant mixture. In some preferred embodiments, the internal pressure of the reservoir temporarily becomes negative when filled with therapeutic fluid having a temperature of about 20° C. or less, such as about 10° C. or less or about 5° C.

A propellant mixture can include two or more propellants, one or more diluent gases, or can two or more propellants and one or more diluent gases. Examples of diluent gases that can be employed include $O_2$, $N_2$, $CO_2$, Ar, Xe, He, and the like.

Any suitable propellant can be used. In some embodiments, a propellant has a vapor pressure in a range from about 10 psig to about 50 psig at 37° C., such as between 20 psig and 24 psig at 37° C. Examples of useful propellants include hydrochlorofluorocarbons (HCFC's) and hydrofluoroalkanes (HFA's) such as HCFC-141b (chemical formula $CCl_2FCH_3$) and HFA-134a (chemical formula $CH_2F\!-\!CF_3$); $C_3F_8$; $SF_6$; and neopentane. Other propellants useful propellants include perfluorocarbons (PFC's) such as perfluorobutane and perfluoropentane; hexafluoro-1,3-butadiene; 1,1,1,2,3,3-hexafluoropropane; octafluoro-2-butene; 1,2-dichlorotetrafluoroethane ($C_2Cl_2F_4$); and 1,1,1,4,4,4-hexafluorobutane.

In selecting a propellant or propellant mixture, care should be taken to avoid adverse interactions between the propellant(s) and components of the infusion device, particularly membranes that separate the propellant chamber from the reservoir chamber. For example, when flexible polymeric membranes are employed, propellants that act as solvents for the polymeric material are preferably avoided. In the alternative, membranes that form the reservoirs can be treated or coated so that they are not reactive with the propellant(s). For example, the surface of the membrane in contact with the propellant(s) can be metallized.

A propellant chamber of an infusion device can include any suitable concentration of propellant. The volume or concentration of the propellant or propellant mixture placed in the propellant chamber can be tuned to achieve a desired internal reservoir pressure.

One example of an implantable infusion device 200 having a refillable reservoir 208 that can be employed in accordance with the teachings presented herein is shown in FIG. 1. The infusion device 200 may be implanted close to the skin 201 of the patient's body 202. The device 200 may include a housing 204 with a bulkhead 206 that divides the interior of the housing into two or more chambers. A reservoir 208 that, in the illustrated embodiment, may be formed by a collapsible bellows 209, is provided and sealed against a lower side of the bulkhead 206. The reservoir 208 may hold therapeutic fluid 211 therein. A propellant chamber 210, in which a propellant or propellant mixture is disposed, surrounds the reservoir 208. As discussed above, the propellant can exert a pressure at least a portion of the structure 209 defining the reservoir 208 such that the pressure in the reservoir 208 is a positive gauge pressure.

In the embodiment depicted in FIG. 1, the device 200 includes a fill port 212 through which a needle 114 of a refill kit, which can include an extension set catheter 106, may enter to refill the reservoir 208. The fill port 212 may include a self-sealing, needle-penetrable septum 214 as is known in the art. The fill port 212 may be coupled to the reservoir 208 via, for example, a refill passageway 216. In addition to the fill port 212, the device 200 may include an outlet port 218 for delivering the therapeutic fluid 211 to the patient. The therapeutic fluid may be transferred from the reservoir 208 to the outlet port 218 via a pumping mechanism 220, such as a piston pump or peristaltic pump. A catheter 222 may deliver the therapeutic substance from the outlet port 218 to the area of the body 202 intended to receive medication. The device 200 may include other components, e.g., a power source 224 and control electronics 226, as is known in the art.

The embodiment of the infusion device depicted in FIG. 1 is one embodiment of an infusion device having a positive pressure reservoir for which methods described herein may be used.

Figure 2:
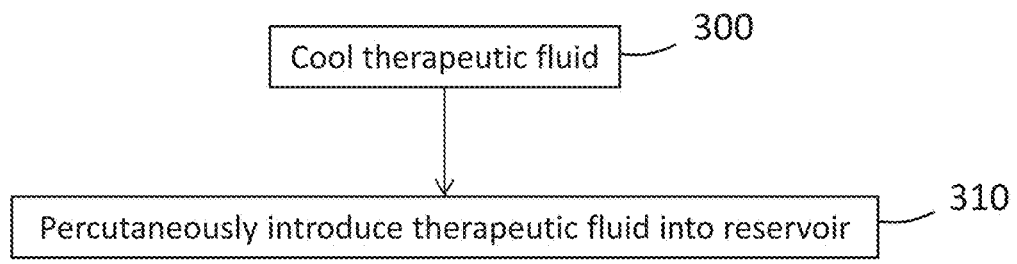
FIG. 2 is a flow diagram of a method in accordance with some embodiments disclosed herein.

Referring now to FIG. 2, an overview of a method for reducing leakage during a refill procedure is shown. The depicted method includes cooling therapeutic fluid (300) and percutaneously introducing the cooled therapeutic fluid into a reservoir of an implanted infusion device (310) to at least partially refill the reservoir. The reservoir can be a positive pressure reservoir. The positive pressure reservoir can be a reservoir upon which pressure is exerted by a propellant.

The therapeutic fluid can be cooled to any suitable amount. For example, the therapeutic fluid can be cooled to about 20° C. or less, such as about 10° C. or less or about 5° C. (e.g., in a range from 2° C. to 8° C.), prior to introduction into the reservoir. For example, the therapeutic fluid can be disposed in a container and cooled in an ice bath or a refrigerator for a sufficient period of time to cool the therapeutic fluid prior to introduction into the reservoir. Preferably, the therapeutic fluid is cooled to an extent sufficient to reduce the temperature in and surrounding the reservoir such that the pressure in the reservoir decreases relative to the pressure in the reservoir at body temperature (about 37° C.). In some embodiments, pressure in the reservoir is decreased from a positive gauge pressure to a negative gauge pressure by introduction of the cooled therapeutic fluid into the reservoir. If the reservoir is a reservoir that has a propellant exerting pressure on the reservoir, e.g. as depicted in FIG. 2, introduction of the cooled therapeutic fluid into the reservoir can cool the propellant and thus reduce the pressure exerted on the reservoir by the propellant.

The decrease in reservoir pressure is temporary, as the temperature of the fluid introduced into the reservoir will equilibrate to body temperature over time. For example, therapeutic fluid at temperature of 4° C. that is introduced into a reservoir of an implanted SynchroMed® II programmable infusion device, which has a 20 ml or 40 ml reservoir capacity depending on the model, will equilibrate to body temperature in about 30 minutes. Substantial decreases in reservoir pressure will typically last only about 5 minutes to about 10 minutes.

The therapeutic fluid can be introduced into the reservoir percutaneously with the use of a refill kit that can include a refill needle and, for example, a syringe. The refill kit can optionally include an extension set catheter to couple the syringe to the needle. In some embodiments, the therapeutic fluid is housed in the syringe as it is cooled prior to percutaneous introduction into the reservoir. The refill needle can be inserted into a refill port that is in communication with the reservoir.

Figure 3:
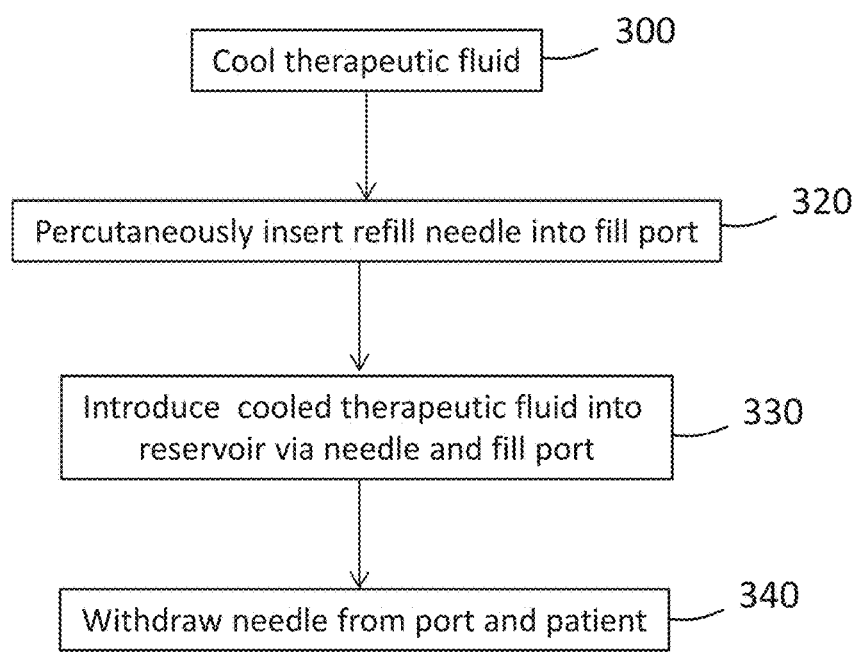
FIG. 3 is a flow diagram of a method in accordance with some embodiments disclosed herein.

Referring now to FIG. 3, an overview of a method for of a method for reducing leakage during a refill procedure is shown. The depicted method includes cooling therapeutic fluid (300), percutaneously inserting a refill needle into a fill port that is in communication with a reservoir (320), percutaneously introducing the cooled therapeutic fluid into the reservoir via the needle and the fill port (330), and withdrawing the needle from the port and the patient (340).

Figure 4:
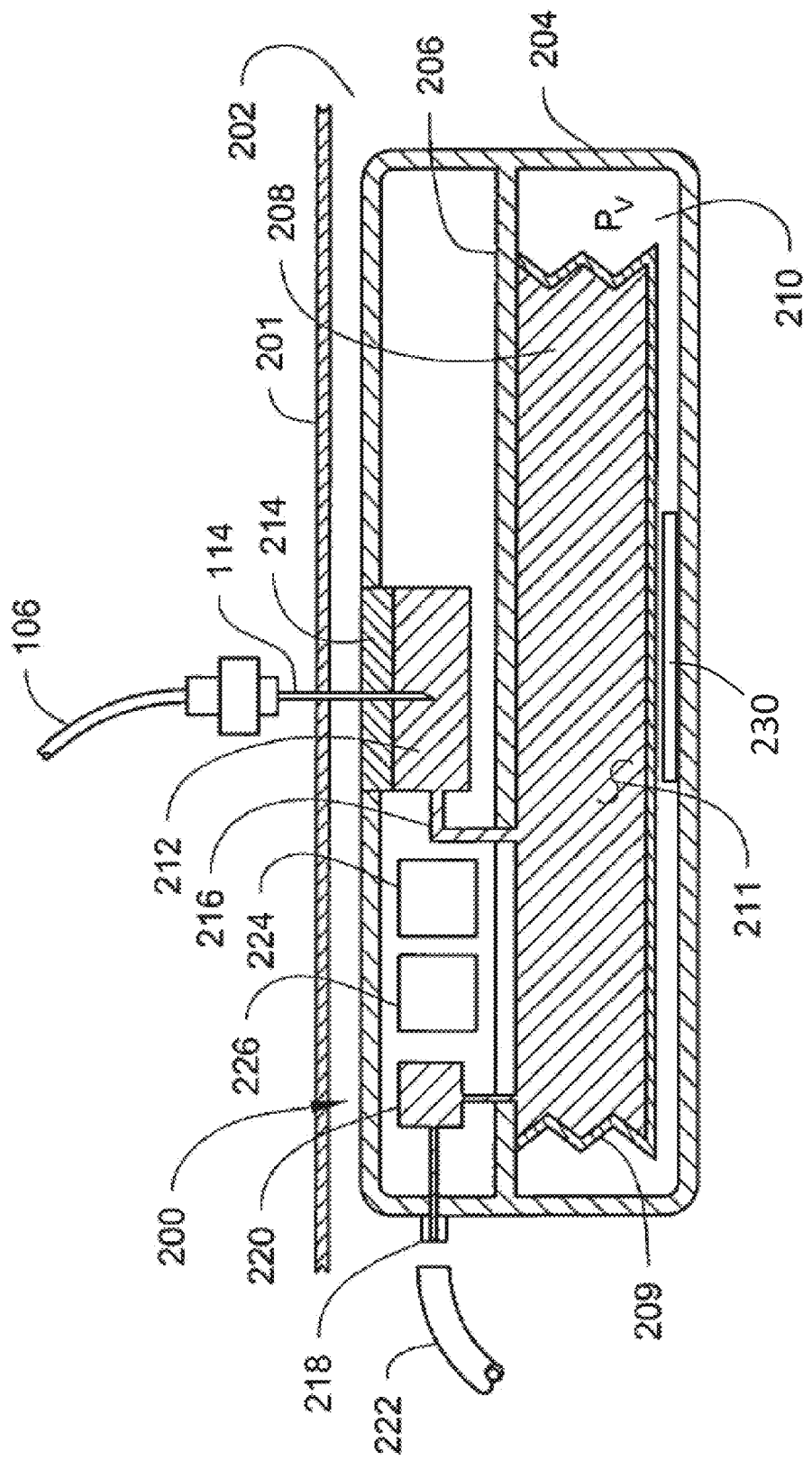
FIG. 4 is a schematic cross-sectional view of an embodiment of an implantable infusion device implanted in a patient.

Referring now to FIG. 4, an embodiment of an implantable infusion device 200 having a cooler 230 positioned and configured to reduce the temperature of a propellant in a propellant chamber 210 is depicted. The embodiment depicted in FIG. 3 is substantially the same as depicted in FIG. 1, except for the cooler 230. For those numbered elements not described with regard to FIG. 3, reference is made to the discussion above regarding FIG. 1. The cooler 230 depicted in FIG. 3 is positioned in the propellant chamber 210, but can be positioned in any suitable location to cool the propellant.

Cooler 230 can be any suitable type of cooler such as a thermoelectric cooler or a vapor-compression refrigerator. Preferably, the cooler is a thermoelectric cooler. Any suitable thermoelectric cooler can be used. For example, the thermoelectric cooler can be a solid-state active heat pump that transfers heat from one side of the cooler (e.g. side facing interior of the propellant chamber 210) to another side of the cooler (e.g., side facing the exterior of the propellant chamber), which can be attached to a heat sink. Such a cooler can use the Peltier effect to create a heat flux between the junction of two different materials. In some embodiments, such a cooler includes two unique semiconductors, such as an n-type semiconductor and a p-type semiconductor, placed thermally in parallel and electrically in series, that are joined to thermally conductive plates on either side of the semiconductors. A DC current can flow through the device to cause heating at one plate and cooling at the other plate.

The cooler 230 can be operably coupled to power source 224 and control electronics 226.

Control electronics 226 can activate cooler 230 prior to or during a refill procedure to cool propellant and reduce pressure in reservoir 208. Preferably, the cooler 230 can cool the propellant to an extent that causes the pressure in the reservoir to become a negative gauge pressure. Once the reservoir 208 has been refilled with therapeutic fluid 211 and refill needle 114 is withdrawn from fill port 212, control electronics 226 can deactivate cooler 230, which will result in an increase reservoir pressure to normal operating pressures over time. In some embodiments, instructions to activate, deactivate, or activate and deactivate cooler 230 can be wirelessly transmitted to device 200 from a device external to patient 202, as generally known in the art. In addition, or alternatively, transmission of data indicating that a refill procedure is about to begin, has begun, has ended, or the like can be transmitted to the device via telemetry.

Various device components can be components as generally known in the art. For example, control electronics may be provided in any suitable form and may, for example, include memory and a processor. Processor may one or more components that can include any one or more of a microprocessor, a controller, a digital signal processor (DSP), an application specific integrated circuit (ASIC), a field-programmable gate array (FPGA), equivalent discrete or integrated logic circuitry, programmable logic circuitry, or the like, and the functions attributed to processor herein may be embodied as hardware, firmware, software or any combination thereof. Memory may store instructions that cause processor to provide the functionality ascribed to programmer herein, and information used by processor to provide the functionality ascribed to programmer herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory may also store information that controls therapy delivery of the infusion device, such as therapeutic fluid delivery rates.

The control electronics may also include components, etc. to operate other features not depicted in the exemplary system such as flow or pressure sensors, alarms, etc.

The control electronics may further include telemetry components configured to receive or send information from the device implanted in a patient. Telemetry may be used to, e.g., allow programming of the infusion rate, infusion times, etc. Telemetry may further be used to provide information from the infusion device such as, e.g., the amount of fluid in the reservoir, etc. Such information may be used to determine whether the reservoir requires refilling, etc. Telemetry can be used to indicate that a refill process has started, will start, or has finished.

Telemetry components can be configured to communicate with another computing device via wireless communication techniques, and may include, for example, an antenna. Examples of local wireless communication techniques that may be employed to facilitate communication between, for example, a programmer and another computing device include RF communication according to the 802.11 or Bluetooth specification sets, or other standard or proprietary telemetry protocols.

The techniques described in this disclosure, including those attributed to infusion device, programmer device, or the like, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Functionality associated with one or more modules or units may be performed by separate hardware or software components, or integrated within common or separate hardware or software components.

Figure 5:
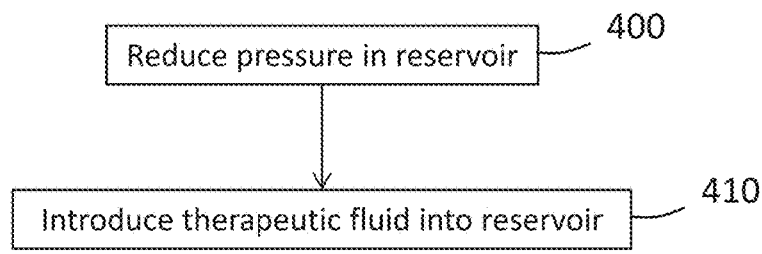
FIG. 5 is a flow diagram of a method in accordance with some embodiments disclosed herein.

Referring now to FIG. 5, an overview of a method for reducing leaks during a procedure to fill or refill a reservoir of an implanted infusion device is depicted. The method includes temporarily reducing pressure in the reservoir (400) and introducing therapeutic fluid into the reservoir (410) having temporarily reduced pressure. The pressure in the reservoir can be reduced prior to introduction of the fluid into the reservoir, while the fluid is introduced into the reservoir, or after the fluid is introduced into the reservoir, but preferably before the refill needle is withdrawn. For the purposes of the present disclosure, a refill procedure extends until a refill needle or equivalent apparatus is withdrawn from the patient.

The pressure in the reservoir can be decreased in any suitable manner. For example, the pressure can be reduced by the introduction of cooled therapeutic fluid into the reservoir, or the pressure can be reduced by activating a cooler to cool propellant in a propellant chamber. In some embodiments, pressure in the chamber is reduced by mechanically expanding the volume of the reservoir.

Figure 6:
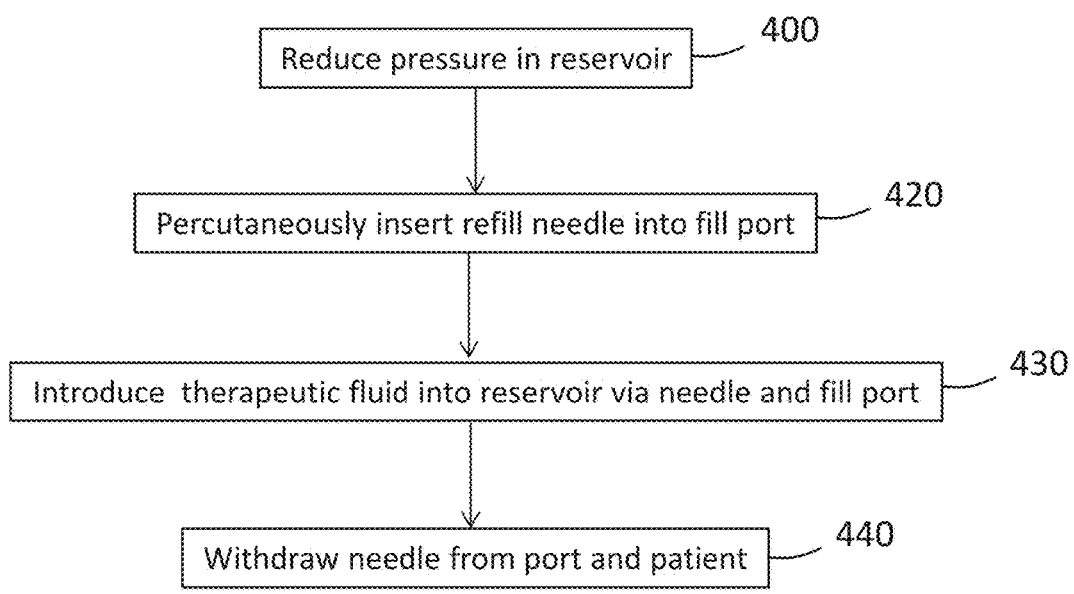
FIG. 6 is a flow diagram of a method in accordance with some embodiments disclosed herein.

Referring now to FIG. 6, an overview of a method for reducing leaks during a procedure to fill or refill a reservoir of an implanted infusion device is depicted. The method includes reducing pressure in the reservoir (400), percutaneously inserting a refill needle into a fill port that is in communication with a reservoir (420), percutaneously introducing the therapeutic fluid into the reservoir via the needle and the fill port (430), and withdrawing the needle from the port and the patient (440).

In various embodiments, the reservoirs of the infusion devices are configured to house a volume of therapeutic fluid sufficient to be delivered over the course of several days, weeks or months. In various embodiments, the reservoirs are configured to hold a volume of therapeutic fluid sufficient to deliver the fluid for a period of time greater than one week, greater than two weeks, or about a month. The reservoirs can have any suitable full working volume. For example, the reservoirs can be configured to house 10 ml, 20 ml, 30 ml, 40 ml, 50 ml or any other suitable volume.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a product, method or the like, means that the components of the, product, method or the like are limited to the enumerated components and any other components that do not materially affect the basic and novel characteristic(s) of the composition, product, method or the like.

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclsoure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

A compound as described herein may contain one or more chiral centers and/or double bonds and, therefore, exist as stereoisomers, such as double-bond isomers (i.e., geometric isomers), enantiomers, or diastereomers. For purposes of the present disclosure, reference to a particular compound encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

When a disclosed compound is named, it is to be understood that solvates (e.g., hydrates) of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include a stoichiometric or non-stoichiometric amount of water bound by non-covalent intermolecular forces.

When a disclosed compound is named, it is to be understood that the compound, including solvates thereof, may exist in crystalline forms, non-crystalline forms or a mixture thereof. The compounds or solvates may also exhibit polymorphism (i.e. the capacity to occur in different crystalline forms). These different crystalline forms are typically known as "polymorphs." It is to be understood that when named, the disclosed compounds and solvates (e.g., hydrates) also include all polymorphs thereof. As used herein, the term "polymorph" means solid crystalline forms of a compound or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it. In addition, one polymorph may spontaneously convert to another polymorph under certain conditions.

When a disclosed compound is named, it is to be understood that clathrates ("inclusion compounds") of the compound or its pharmaceutically acceptable salts, solvates or polymorphs are also included. As used herein, the term "clathrate" means a compound of the present invention or a salt thereof in the form of a crystal lattice that contains spaces (e.g., channels) that have a guest molecule (e.g., a solvent or water) trapped within.

INCORPORATION BY REFERENCE

Any patent or non-patent literature cited herein is hereby incorporated herein by reference in its entirety to the extent that it does not conflict with the disclosure presented herein.

SUMMARY OF VARIOUS ASPECTS

A number of aspects of methods, devices, systems and kits are disclosed herein. A summary of some selected aspects is provided below.

A first aspect is a method. The method comprises percutaneously introducing a therapeutic fluid into a reservoir of an implantable medical device, wherein the temperature of the therapeutic fluid being introduced is 20° C. or less.

A second aspect is a method of the first aspect, wherein the temperature of the therapeutic fluid being introduced is 10° C. or less.

A third aspect is a method of the first aspect, wherein the temperature of the therapeutic fluid being introduced is about 5° C.

A fourth aspect is a method of any one of aspects 1-3, further comprising chilling the therapeutic fluid to the temperature less than 20° C. prior to introducing the therapeutic reservoir into the reservoir.

A fifth aspect is a method of any one of aspects 1-4, wherein the therapeutic fluid comprises a therapeutic agent for treating pulmonary arterial hypertension.

A sixth aspect is a method according to any one of aspects 1-5, wherein the therapeutic fluid comprises a therapeutic agent selected from the group consisting of an endothelin receptor antagonist, a phosphodiesterase type 5 inhibitor, and a prostanoid.

A seventh aspect is a method according to any one of aspects 1-6, wherein the therapeutic fluid comprises a therapeutic agent selected from the group consisting of bosentan, silendafil citrate, iloprost, treprostinil sodium, and epoprostenol sodium.

An eight aspect is a method according to any one of aspects 1-7, wherein the therapeutic fluid comprises treprostinil sodium.

A ninth aspect is a method according to any one of aspects 1-8, wherein the reservoir of the implanted infusion device is a positive pressure reservoir.

A tenth aspect is a method according to the ninth aspect, wherein the infusion device comprises a propellant exerting pressure on the reservoir.

An eleventh aspect is a method. The method includes decreasing pressure in a reservoir of an implanted infusion device; and introducing a therapeutic fluid into the reservoir.

A twelfth aspect is a method according to the eleventh aspect, wherein introducing the therapeutic fluid into the reservoir temporarily decreases the pressure in the reservoir.

A thirteenth aspect is a method according to the eleventh aspect, wherein the pressure in the reservoir is decreased prior to introducing the therapeutic agent into the reservoir.

A fourteenth aspect is a method according to any one of aspects 11-13, wherein decreasing the pressure in the reservoir comprises expanding the volume of the reservoir.

A fifteenth aspect is a method according to any one of aspects 11-14, wherein the infusion device comprises a propellant exerting pressure on the reservoir, and wherein decreasing the pressure in the reservoir comprises cooling the propellant.

A sixteenth aspect is a method according to the fifteenth aspect, wherein the infusion device comprises a thermoelectric cooling device in contact with the propellant, and wherein cooling the propellant comprises activating the thermoelectric cooling device.

A seventeenth aspect is method according to any of aspects 11-16, wherein the therapeutic fluid comprises a therapeutic agent for treating pulmonary arterial hypertension.

An eighteenth aspect is a method according to any of aspects 11-17, wherein the therapeutic fluid comprises treprostinil sodium.

A nineteenth aspect is an implantable medical infusion device. The device comprises a chamber; and a variable volume reservoir having an exterior surface and defining a variable interior volume for containing therapeutic fluid. At least a portion of the reservoir is disposed in the chamber. The device further comprises a propellant disposed in the chamber and configured to exert a pressure on the at least a portion of the exterior surface of the reservoir; and a thermoelectric cooling device positioned and configured to cool the propellant in the chamber.

A twentieth aspect is an implantable medical infusion device of the nineteenth aspect, further comprising a fill port assembly, the fill port assembly comprising (i) a port in communication with the reservoir and configured to receive a refill needle; and (ii) a septum disposed across the port.

A twenty-first aspect is a method for reducing incidence of side effects associated with refilling a reservoir of an implantable infusion device with treprostinil sodium. The method comprises identifying a patient having an implanted infusion device. The infusion device comprises a positive pressure reservoir and comprises a propellant exerting pressure on the reservoir. The patient is receiving treatment with a fluid therapeutic comprising treprostinil sodium via infusion of the therapeutic fluid from the reservoir of the implanted infusion device into the patient. The method further comprises percutaneously removing the therapeutic fluid from the reservoir, if any of the therapeutic fluid remains in the reservoir. The method also comprises percutaneously refilling the reservoir with fresh therapeutic fluid comprising treprostinil sodium, wherein the temperature of the fresh therapeutic fluid being introduced is less than 10° C.

Thus, systems, devices and methods for LEAK REDUCTION DURING IMPLANTABLE INFUSION DEVICE REFILL are described. Those skilled in the art will recognize that the preferred embodiments described herein may be altered or amended without departing from the true spirit and scope of the disclosure, as defined in the accompanying claims. In the detailed description above several specific embodiments of infusion devices and systems and refill methods are disclosed. It is to be understood that other embodiments are contemplated and may be made without departing from the scope or spirit of the present disclosure. The detailed description, therefore, is not to be taken in a limiting sense. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

The invention claimed is:

1. A method comprising:
   percutaneously introducing a therapeutic fluid into a reservoir of an implantable medical device, wherein the temperature of the therapeutic fluid being introduced is 10° C. or less, wherein the therapeutic fluid comprises treprostinil sodium, and
   wherein introducing the therapeutic fluid in the reservoir decreases the pressure in the reservoir from a positive gauge pressure to a negative gauge pressure.

2. The method according to claim 1, wherein the temperature of the therapeutic fluid being introduced is about 5° C.

3. The method according to claim 1, further comprising chilling the therapeutic fluid to the temperature of 10° C. or less prior to introducing the therapeutic fluid into the reservoir.

4. The method according to claim 1, wherein the reservoir of the implantable medical device is a positive pressure reservoir.

5. The method according to claim 4, wherein the implantable medical device comprises a propellant exerting pressure on the reservoir.

6. The method according to claim 1, wherein the therapeutic fluid is percutaneously introduced into the reservoir of the implantable medical device via a needle and a fill port, wherein the method further comprises:
   withdrawing the needle from the fill port; and
   reducing subcutaneous leakage of therapeutic fluid as a result of the temperature of the therapeutic fluid being introduced at 10° C. or less as compared to the therapeutic fluid at 37° C.

7. The method according to claim 1, wherein introducing the therapeutic fluid in the reservoir temporarily decreases the pressure in the reservoir.

8. A method comprising:
   percutaneously introducing a therapeutic fluid into a reservoir of an implantable medical device via a needle and a fill port, wherein the temperature of the therapeutic fluid being introduced is 10° C. or less, wherein introducing the therapeutic fluid in the reservoir decreases the pressure in the reservoir from a positive gauge pressure to a negative gauge pressure;

withdrawing the needle from the fill port; and reducing subcutaneous leakage of therapeutic fluid as a result of the temperature of the therapeutic fluid being introduced at 10° C. or less as compared to the therapeutic fluid at 37° C., wherein the therapeutic fluid comprises treprostinil sodium.

9. The method according to claim 8, wherein introducing the therapeutic fluid in the reservoir temporarily decreases the pressure in the reservoir.

10. A method comprising:

percutaneously introducing a therapeutic fluid into a reservoir of an implantable medical device, wherein the temperature of the therapeutic fluid being introduced is about 5° C., wherein the therapeutic fluid comprises treprostinil sodium, and wherein the reservoir of the implantable medical device is a positive pressure reservoir, and wherein introducing the therapeutic fluid in the reservoir decreases the pressure in the reservoir from a positive gauge pressure to a negative gauge pressure.

11. The method according to claim 10, wherein the implantable medical device comprises a propellant exerting pressure on the reservoir.

12. The method according to claim 10, wherein the therapeutic fluid is percutaneously introduced into the reservoir of the implantable medical device via a needle and a fill port, wherein the method further comprises:

withdrawing the needle from the fill port; and reducing subcutaneous leakage of therapeutic fluid as a result of the temperature of the therapeutic fluid being introduced at about 5° C. as compared to the therapeutic fluid at 37° C.

13. The method according to claim 10, wherein introducing the therapeutic fluid in the reservoir temporarily decreases the pressure in the reservoir.

* * * * *